(12) United States Patent
Giorgi et al.

(10) Patent No.: US 6,515,012 B2
(45) Date of Patent: Feb. 4, 2003

(54) PROCESS FOR THE PREPARATION OF ZOFENOPRIL CALCIUM SALT

(75) Inventors: Raffaello Giorgi, deceased, late of Pomezia (IT); by Rosaria Pirari, legal representative, Pisa (IT); by Alberta Giorgi, legal representative, Milan (IT); Antonio Giachetti, Pomezia (IT); Carlo Mannucci, Pomezia (IT); Anita Falezza, Pomezia (IT)

(73) Assignee: Menarini Ricerche S.p.A., Pomezia (IT)

( * ) Notice: Subject to any disclaimer, the term of this patent is extended or adjusted under 35 U.S.C. 154(b) by 0 days.

(21) Appl. No.: 10/155,129

(22) Filed: May 28, 2002

(65) Prior Publication Data

US 2002/0156293 A1 Oct. 24, 2002

Related U.S. Application Data

(62) Division of application No. 09/762,054, filed as application No. PCT/EP99/05461 on Jul. 30, 1999.

(30) Foreign Application Priority Data

Aug. 4, 1998 (IT) ..................... MI98A001833

(51) Int. Cl.$^7$ ............................................. A61K 31/40
(52) U.S. Cl. ..................................................... 514/423
(58) Field of Search ......................................... 514/423

(56) References Cited

U.S. PATENT DOCUMENTS

| 4,105,776 A | 8/1978 | Ondetti et al. |
| 4,154,935 A | 5/1979 | Ondetti et al. |
| 4,316,906 A | 2/1982 | Ondetti et al. |

OTHER PUBLICATIONS

XP–002125355, John Krapcho et al. "Angiotensin–Converting Enzyme Inhibitors. Mercaptan, Carboxyalkyl Dipeptide, and Phosphinic Acid Inhibitors Incorporating 4–Substituted Prolines", Journal of Medicinal Chemistry, 1998, pp. 1148–1160.

Primary Examiner—Raymond Henley, III
(74) Attorney, Agent, or Firm—Young & Thompson

(57) ABSTRACT

A process for the preparation of polymorph A of zofenopril calcium salt in substantially pure form, which comprises: 1) reaction of S(–)-3-benzoylthio-2-methylpropanoic acid chloride with cis-4-phenylthio-L-proline in water at pH ranging from 9.0 to 9.5 and recovery of zofenopril in the acidic form; b) salification of acid zofenopril with a poyassium salt in alcoholic solution, and recovery of the resulting potassium salt; c) conversion of the potassium salt to the calcium salt by addition of zofenopril potassium salt aqueous solution to a CaCl$_2$ aqueous solution at a temperature of 70–90° C. with simultaneous seeding to promote the precipitation of polymorph A.

6 Claims, 4 Drawing Sheets

PROCESS FOR THE PREPARATION OF ZOFENOPRIL CALCIUM SALT

This is a divisional application of U.S. application Ser.No. 09/762,054 filed Jun. 4, 2001 which is a 371 of PCT/EP99/05461 filed Jul. 30, 1999.

FIELD OF THE INVENTION

The present invention relates to a novel process for the preparation of zofenopril calcium salt. This compound can reportedly exist in the solid state in at least two polymorph forms, named A and B; the novel synthetic process according to the invention yields zofenopril calcium salt only in the form of polymorph A, substantially pure from the form B.

BACKGROUND OF THE INVENTION

Zofenopril, [(4S)-(2S)-3-(benzoylthio)-2-methylpropionyl-4 (phenylthio)-L-proline] calcium salt, has the following formula I

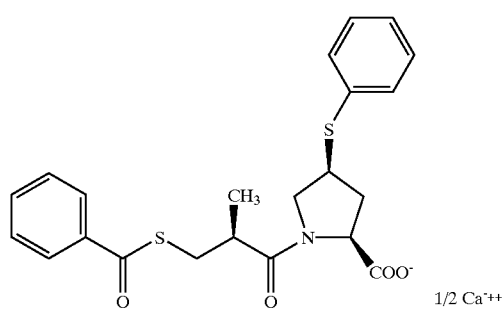

(1)

Zofenopril and other analogues thereof, have been described in U.S. Pat. No. 4,316,906. The synthesis used to obtain the calcium salt is schematized in Scheme I and it substantially comprises three steps:
a) condensation between cis-4-phenylthio-L-proline and D-3-(benzoylthio)2-methylpropionyl chloride in aqueous solution keeping pH at values of 8~8.5 by addition of 5N sodium hydroxide; subsequent acidification with HCl, extraction with isobutyl acetate and concentration of the extracts, washing with saline solution, to give (4S)-1-[(2S)-3-(benzoylthio)-2-methylpropionyl]-4-(phenylthio)-L proline;
b) treatment of the resinous material from the previous step in isopropanol solution with potassium 2-hethylhexanoate to obtain the corresponding potassium salt;
c) dissolution of the potassium salt in water to a 57% concentration and very slow addition, with simultaneous seeding, of a slight excess of a 2N calcium chloride aqueous solution to precipitate the desired calcium salt. The resulting product is washed thoroughly with water, dried under vacuum at a comparatively high temperature to give the desired calcium salt as dry powder; melting point about 2500°. Alternatively:
d) (4S)-1-[(2S)-3-(benzoylthio)-2-methylpropionyl1-4-(phenylthio)-L-proline is dissolved in ethanol and treated with the same volume of an aqueous suspension containing one equivalent of CaO; after removing ethanol and subsequently washing with ether, the aqueous suspension is freeze-dried to obtain the calcium salt with melting point 235–237° (dec.).

The existence of polymorphs in the case of zofenopril calcium salt had been clearly defined in J. Pharmaceutical & Biomedical Analysis, 1994, Vol 12, pp. 173–177 which stated that tablets of zofenopril calcium salt prepared with polymorph A or with polymorph B could not be differentiated on the basis of the their dissolution rate, but reported no chemical-physical characterizations of the two polymorphs. The phenomenon of polymorphism, however, makes it difficult to prepare different batches of zofenopril calcium always having the same chemical-physical characteristics, which is a requisite indispensable to assure the maximum reproducibility for scientific, regulatory and therapeutical purposes.

It has now been found that polymorph A is more resistant to compression and/or micronisation than polymorph B, and therefore polymorph A is much more industrially preferable than polymorph B for the preparation of pharmaceutical formulations in the solid form, such as tablets; it is also evident, in view of what stated above, that polymorph A substantially pure from polymorph B is industrially preferred.

On the other hand, the previously known processes for the preparation of zofenopril calcium salt could not provide polymorph A sufficiently pure from polymorph B. In fact, the synthesis described in U.S. Pat. No. 4,316,906 (cited above at points a, b and c) mainly yields polymorph A, but also polymorph B in percentages very variable and never below 20%; moreover, the alternative synthesis described in U.S. Pat. No. 4,316,906 (cited at point d) gives a partially amorphous product, with very variable characteristics in which polymorph A, when present, is in concentrations much lower than those obtained in the preceding process.

These problems have been solved by the process of the invention which makes it possible to prepare a product in which only and always polymorph A substantially pure from polymorph B is present.

SUMMARY OF THE INVENTION

Figure 1A:
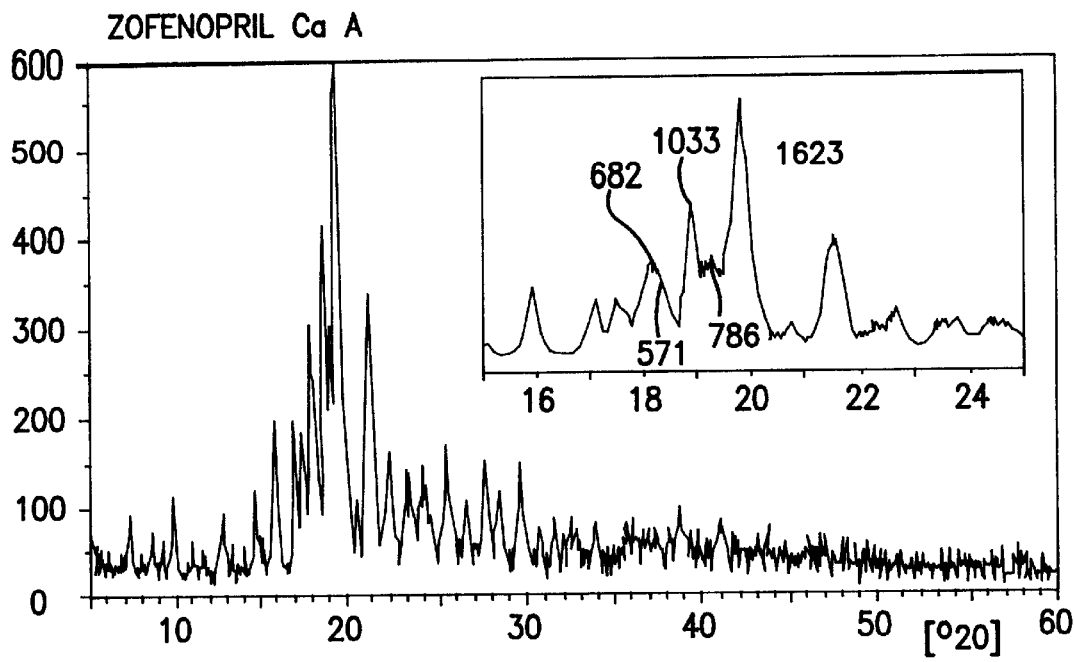
FIG. 1 shows X ray diffractograms for Zofenopril Calcium polymorphs A and B.

The process for the preparation of substantially pure polymorph A from zofenopril calcium salt comprises:
a) reaction of S(−)-3-benzoylthio-2-methylpropanoic acid chloride and cis-4-phenylthio-L-proline in water at pH ranging from 9.0 to 9.5 and recovery of zofenopril in the acidic form;
b) salification of acid zofenopril with a potassium salt in alcoholic solution, and recovery of the resulting potassium salt;
c) conversion of the potassium salt to calcium salt by addition of an aqueous solution of zofenopril potassium salt to a $CaCl_2$ aqueous solution at 70–90° C. with simultaneous seeding to promote the precipitation of polymorph A.

DETAILED DESCRIPTION OF THE INVENTION

The process of the invention is schematized in the Scheme below.

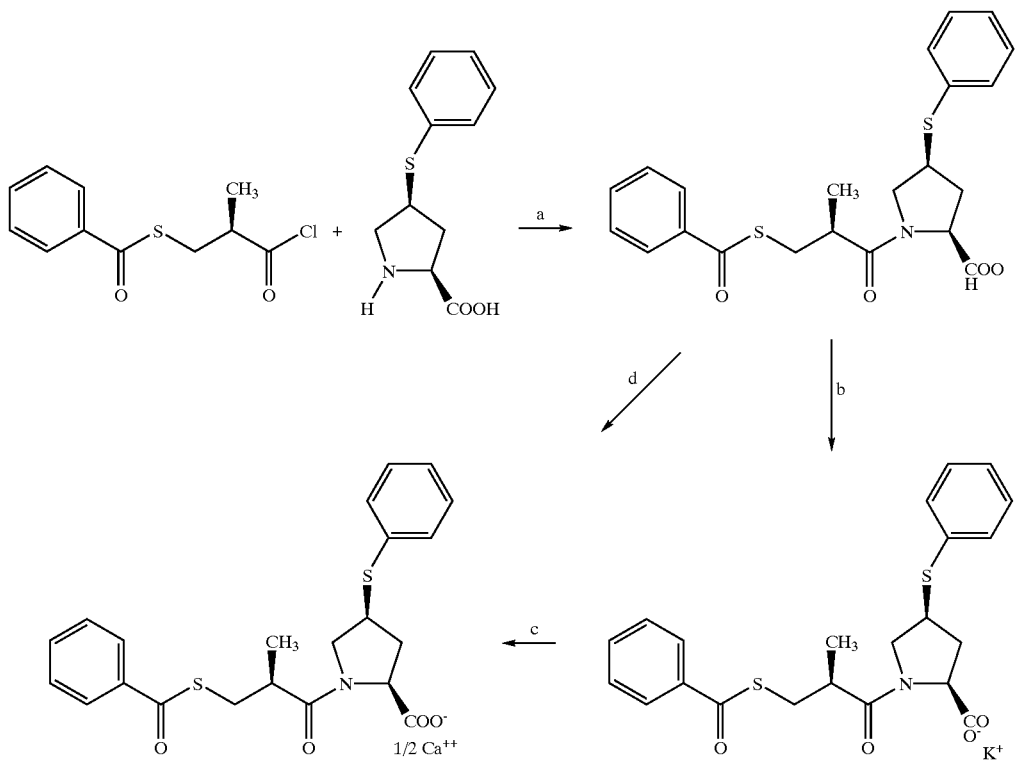

In step a), S-(−)-3-benzoylthio-2-methylpropanoic acid is treated with a chlorinated agent, preferably oxalyl chloride or thionyl chloride, at temperatures from −10° to +50° C., preferably at 20–25° C., in an aprotic organic solvent, to give the corresponding acid chloride. The volatile components of the reaction mixture are removed under vacuum and the resulting oil is dissolved in an aprotic organic solvent, preferably methylene chloride, ethyl acetate, isobutyl acetate, and slowly added to a solution of cis-4-phenylthio-L-proline in water at pH 9–9.5, preferably 9.5, at temperatures from −10° to +50° C., preferably 20–25° C. pH is kept at the desired values by addition of a sodium hydroxide solution.

After completion of the addition, the mixture is stirred at room temperature for a time from 15 minutes to 4 hours, preferably 30 minutes, keeping pH at the desired value (9–9.5). The reaction mixture is then acidified with concentrated hydrochloric acid and extracted with an organic solvent, which is subsequently evaporated off to obtain zofenopril free acid.

The pH at which the condensation takes place should be considered a critical parameter of the synthesis as it remarkably affects the purity of the final product and the total yield of zofenopril potassium salt (step b): it has, in fact, been observed that yields decrease at pH values below 9 and that the benzoyl group of the thioester is hydrolysed at values above 9.5.

Furthermore, the selected pH does not compromise the isomeric purity of the starting material and of the resulting zofenopril, therefore the stereomeric composition of zofenopril free acid depends on the stereomeric purity of the starting material.

In step b), the above obtained acid is dissolved in an alcoholic solvent, preferably isopropyl alcohol, and treated with a solution in the same alcohol containing an equivalent amount of a potassium organic salt, preferably potassium 2-ethylhexanoate. The zofenopril potassium salt is collected by centrifugation, washed and dried.

Zofenopril potassium salt is a very important intermediate as the purity of the final zofenopril calcium salt, due to its insolubility, remarkably depends on the purity of the corresponding potassium salt.

In fact, in case zofenopril contains unacceptably high levels chemical and/or stereomeric impurities, its potassium salt can be purified by selective crystallization from isopropanol/water.

Finally, in step c), the potassium salt is dissolved in water and added to a calcium chloride aqueous solution, kept at a temperature of 70–90° C., preferably 80–85° C. The precipitation takes place by seeding. The calcium salt is collected by centrifugation and washed thoroughly with deionized water until washing water is substantially free from chloride ions, according to the $AgNO_3$ test or to conductivity measurements.

The described synthetic process yields batches of zofenopril calcium salt as polymorph A substantially pure from polymorph B or anyway with percentages of the latter around the lower limit of detectability (below 7%).

The samples of zofenopril calcium salt obtained according to the process of the invention are stable and show no interconversion to polymorph B; in fact, samples stored for 3 years at 25° C. and 60% relative humidity or samples stored for 6 months at 40° C. and 75% relative humidity show a negligible percentage of polymorph B (below 7%) which remains unchanged in time.

A further object of the invention are therefore the pharmaceutical compositions containing as active ingredient substantially pure zofenopril calcium salt Polymorph A, for example with residual percentages of polymorph B below 15%, preferably below 7%.

The invention is illustrated in the following Examples.

EXAMPLE 1 a) Zofenopril: (S)-3-benzoylthio-2-methylpropanoic acid (6.0 kg; 28.8 M) is dissolved in methylene chloride, in the presence of a catalytic amount of DMF. This solution is slowly added with oxalyl chloride (2.79 L), keeping temperature at 20–25° C. After completion of the addition the reaction mixture is heated at 35–38° C. for at least 1.5 hours. The solution is then concentrated under vacuum at 35–45° C. and then cooled to 15–20° C. under nitrogen atmosphere. The resulting oil, (S)-3-benzoylthio-2-methylpropanoyl chloride, is dissolved in isobutyl acetate and slowly added to an aqueous solution containing cis-4-phenylthio-L-proline (6.5 kg; 29.1 M) kept at pH 9–9.5 by continuous addition of a 20% sodium hydroxide solution. During the addition the temperature is steadily kept at 20–25° C. At the end of the addition the mixture is stirred for ½ hour at pH 9.5 to complete the reaction. The reaction mixture is acidified to pH 1.8–2.0 with concentrated hydrochloric acid and the two phases are separated. The organic phase is evaporated off to obtain zofenopril free acid.

b) Zofenopril potassium salt: the free acid obtained above is dissolved in the minimum amount of isopropanol at a temperature of 58–60° C. and added with a concentrated solution of potassium 2-ethyl hexanoate (5.3 kg; 2.9.1 M) in isopropanol. The mixture is kept under stirring for not less than 8 hours, during which time temperature is left to slowly decrease to 20–25° C. The precipitated zofenopril potassium salt is collected by centrifugation, washed with isopropanol and dried under vacuum at 45–50° C. for at least 8 hours. Yield 96%.

c) Zofenopril calcium salt, Polymorph A: 23.32 kg of zofenopril potassium salt are dissolved in 180 L of water. The resulting solution is purified by filtration, washing all the apparatus used with a further 19 L of water, which are then added to the above solution. 7.4 kg of $CaCl_2$ dihydrate are dissolved in 324 L of water. The solution is purified by filtration, washing all the apparatus used with a further 137 L of water which are added to the filtered solution. The $CaCl_2$ solution is heated to 80–850° C. and added with 6.5 L of the zofenopril potassium salt solution, seeding it with crystals of zofenopril calcium Polymorph A obtained above. The resulting suspension is stirred for 30 min and added with the residual solution of zofenopril potassium salt during a time of 2.50 hours keeping temperature at 80–85° C. At the end of the addition, the suspension is stirred for 30 min and centrifuged when still warm. The solid residue is washed with water until a negligible concentration of chloride ions is detected on the effluent, based on the $AgNO_3$ test or on conductivity measurements. The residue is then dried under vacuum at 40° C. to a water content lower than 3%. Yield higher than 96%. Polymorph B cannot be detected in the product.

EXAMPLE 2

Synthesis of Polymorph B

Starting from zofenopril potassium salt, polymorph B substantially pure from polymorph A can be obtained by the following process, an example of which is the following: A solution of zofenopril potassium salt (0.27 M) is sprayed in lukewarm water (55° C.), while adding a calcium chloride solution (1.17 M); the solutions are such that the total amounts of zofenopril potassium salt and calcium chloride are equimolar. The resulting suspension containing the slurry product is heated at 85° C. for 12–14 hours to obtain a complete conversion to polymorph B. After cooling at about 25° C., the product is filtered, washed with water until it is substantially free from chloride ions, according to conductivity measurements. The filtrate is then dried under vacuum. Yields higher than 90%.

EXAMPLE 3

Characterization of the Polymorphs

Polymorphs A and B of zofenopril calcium salt can easily be differentiated by means of X ray diffractometry (DXR) and/or scanning electron microscopy (SEM) techniques.

No interconversions between the two polymorphs could be observed.

Figure 1B:
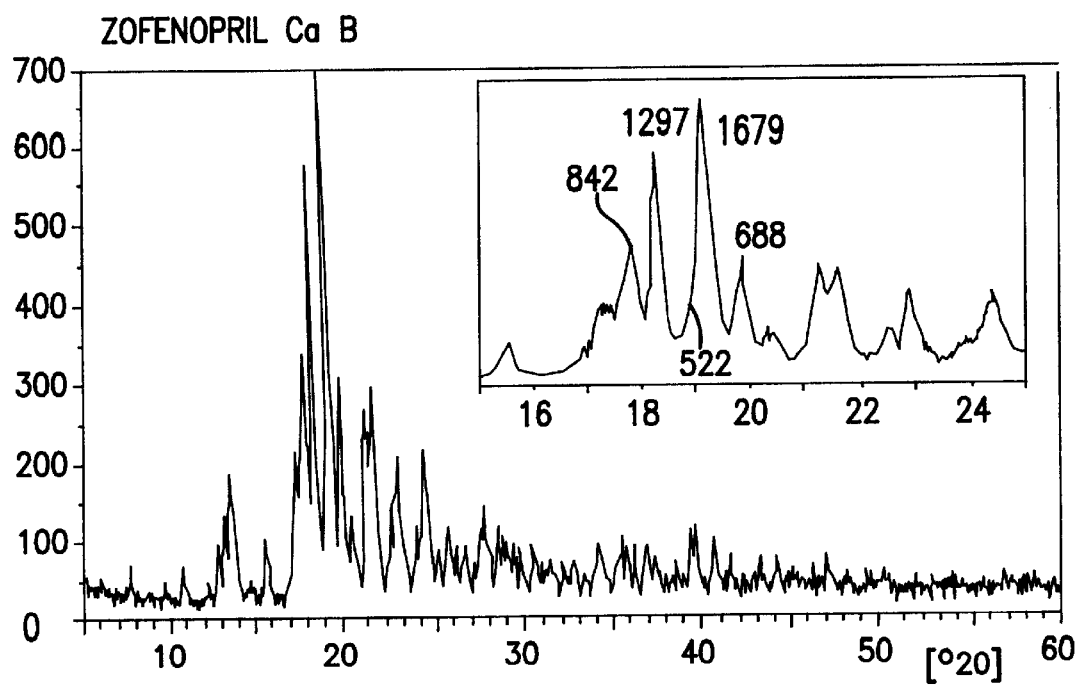

DRX: The diffraction spectra were recorded on powder of the two samples, using a PW-1710 diffractometer in the $2\theta$ range from 0° to 60°. About 10 mg of sample were suspended in petroleum ether and placed on a glass slide which was placed on the sample holder of the instrumentation. Diffractograms of the two polymorphs markedly differ both in the number of diffraction peaks, and in their position in the spectrum. The spectrum region in which the differences are more significant is that ranging from $2\theta=15$ to $2\theta=25$ (FIG. 1) and the quantitative evaluation of the two polymorphs in the analysis of mixtures thereof has been based on this very region.

SEM: Samples were metalized with gold and photographed at various magnitudes using a scanning electron microscope.

The two polymorphs have different characteristics in both their morphology and particle sizes.

Polymorph A is in the form of apparently lamellar aggregates with particle sizes not exceeding 50 μm. Polymorph B is in the form of spherical macroaggregates of diameter ranging from 0.2 to 1.0 mm. Magnification of the surface of the spheres shows prismatic particles with evident rosette growth.

Figure 4:
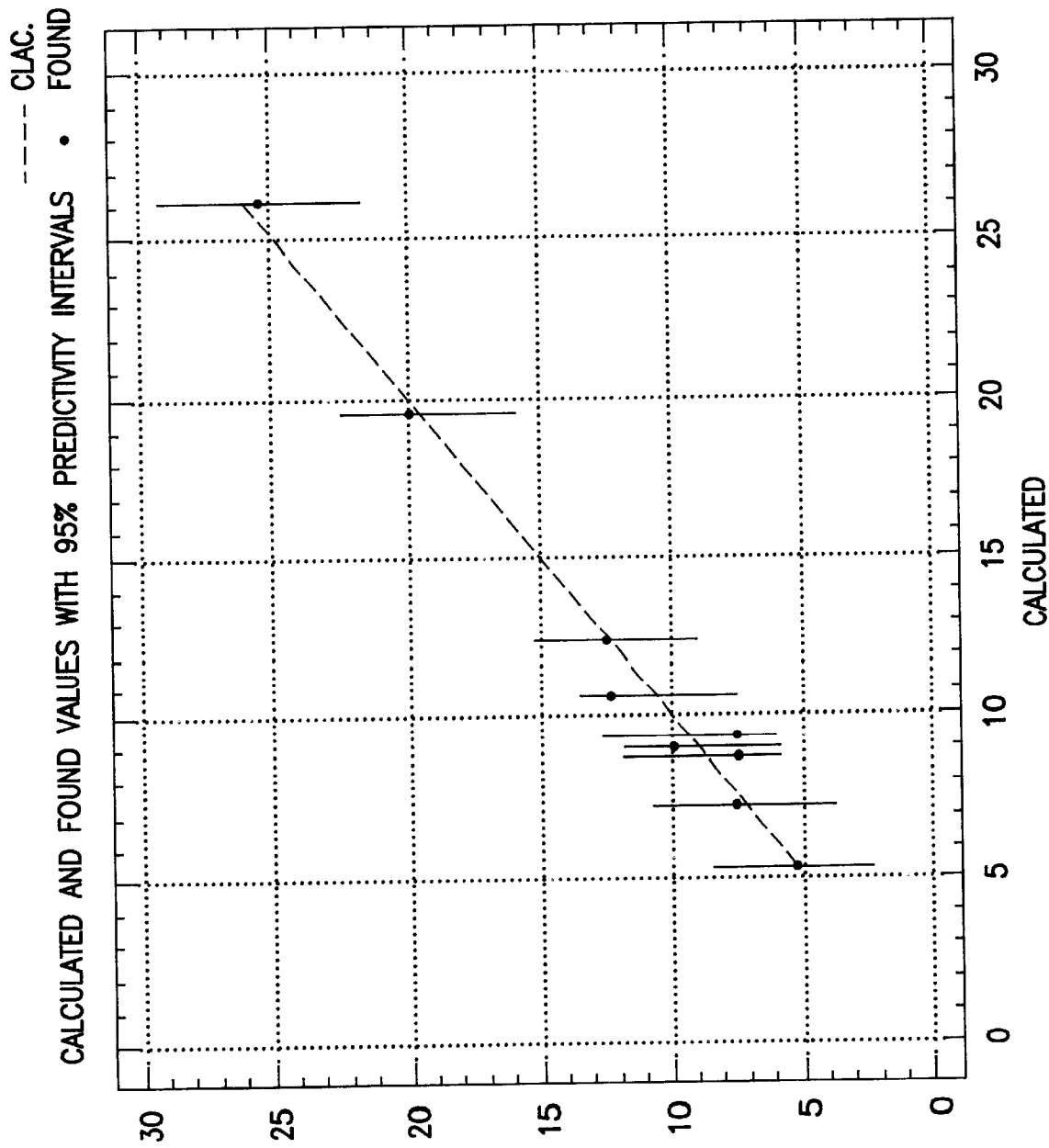
FIG. 4 shows the relationship between a calculated regression equation and observed values for the percentage of polymorph B in samples of polymorph A.

Determination of polymorph B in the samples of Polymoroh A : The percentage of polymorph B in samples of Polymorph A can easily be evaluated by observation of the X diffractograms (DRX). The region used for the analysis was that for $2\theta$ ranging from 15 to 25. In this region, three peaks were evidenced, respectively I with $2\theta=18.4$, II with $2\theta=19.2$ and III with $2\theta=19.9$, and the relative intensities I/III and II/III of various Polymorph A samples containing known amounts of Polymorph B (not above 30%) were measured. A regression equation was thereby obtained, which correlates the intensities of peaks I and II relating to peak III with the percentage of polymorph B present in the samples. The precision and the accuracy of the results obtainable with the above mentioned equation were good and, based on the confidence limits, the minimum amount of polymorph B detectable in polymorph A could be evaluated to be <7%. FIG. 4 reports the relationship between the above mentioned values based on the thus calculated regression equation and the observed values.

Stability to micronisation of Polymorphs

Figure 2A:
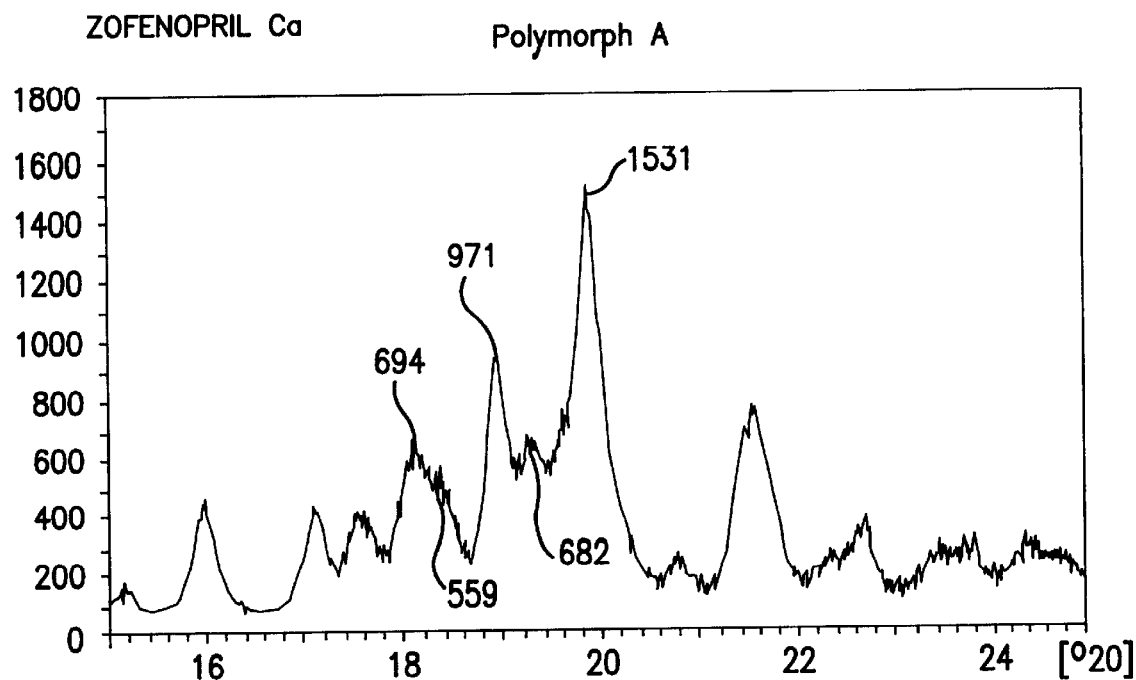
FIGS. 2 and 3 show X ray diffractograms for Zofenopril Calcium polymorphs A and B before and after being subject to grinding using a Retsch MM2 ball micronizer.
Figure 2B:
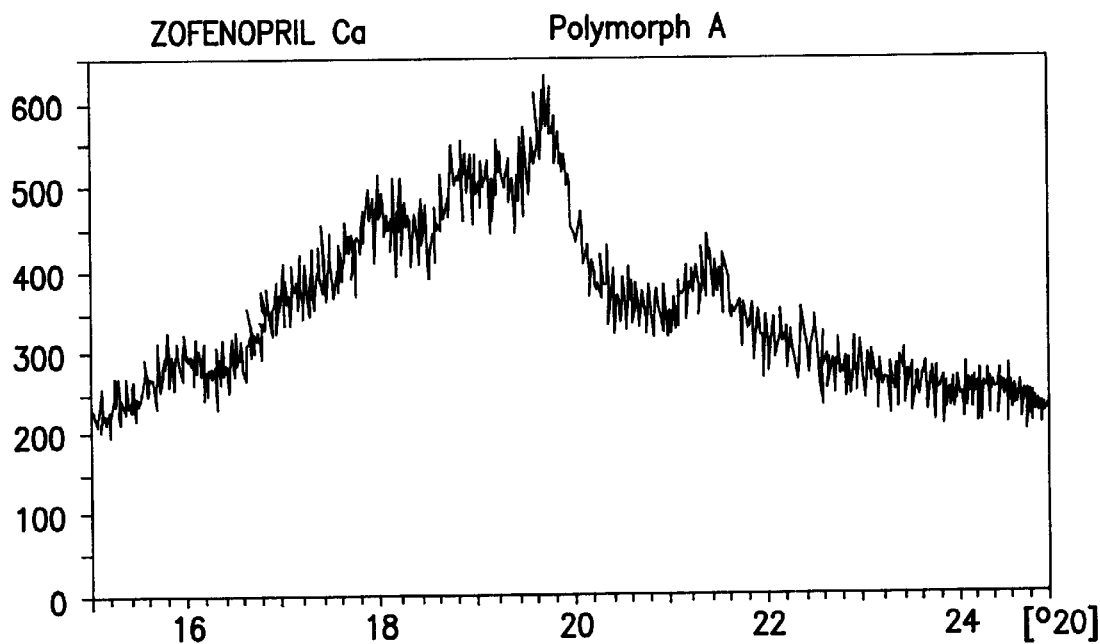
Figure 3A:
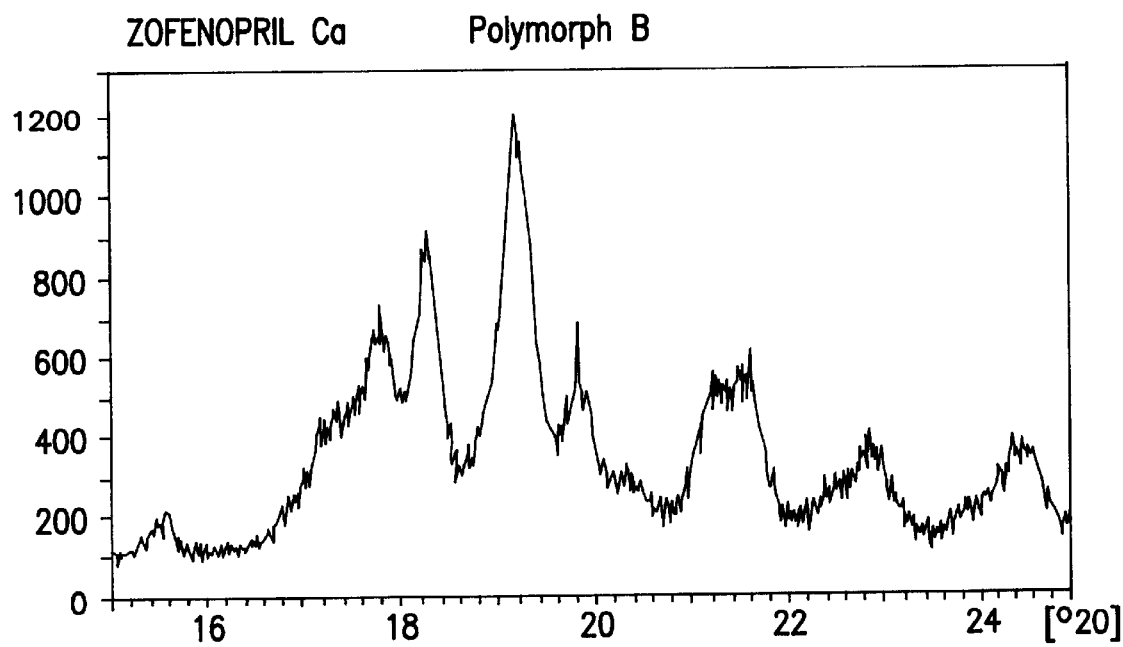
Figure 3B:
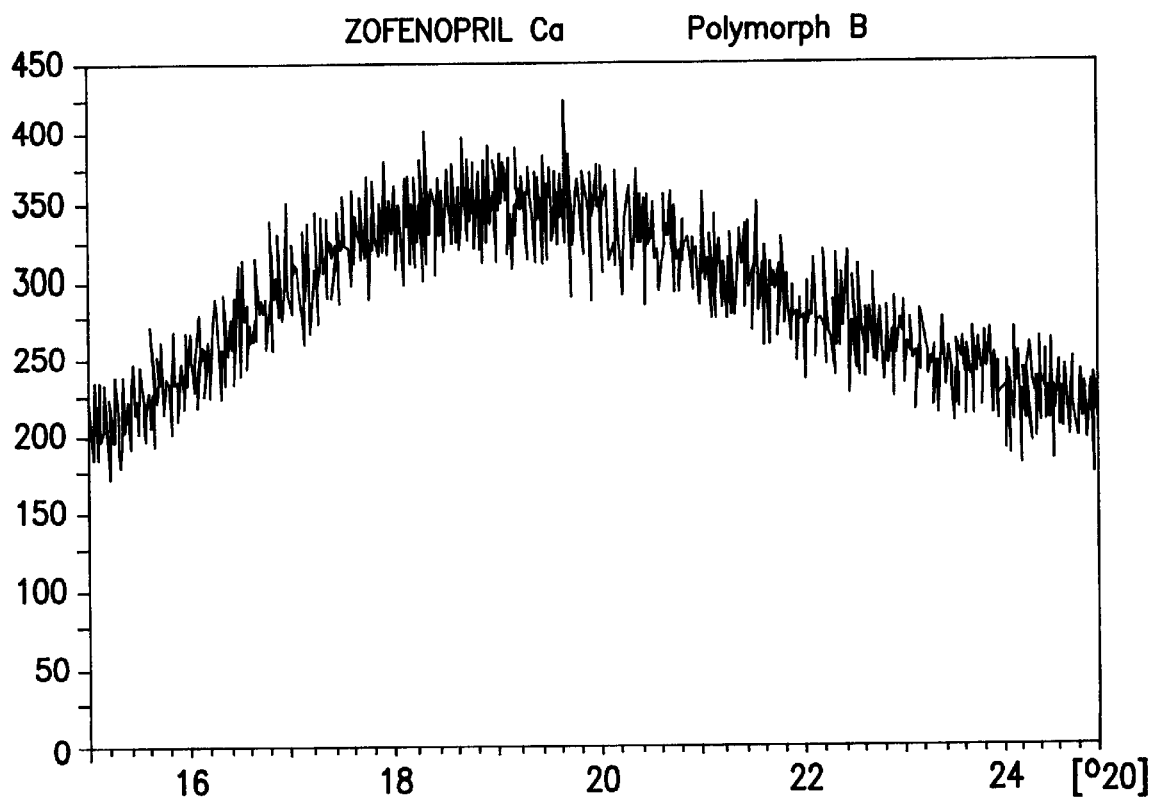

The two polymorphs were ground in drastic conditions using a Retsch MM2 ball microniser loaded with 200 mg of the sample, operating at 80 vibrations/min for a time of 15 minutes, and they showed different stabilities under the same experimental conditions. In fact, according to DRX, polymorph A still keeps the crystalline structure after the treatment (FIG. 2), whereas polymorph B completely loses its crystalline structure changing into a completely amorphous solid phase (FIG. 3).

What is claimed:

1. A pharmaceutical composition containing as active ingredient substantially pure zofenopril calcium salt Polymorph A.

2. A pharmaceutical composition containing as active ingredient polymorph A of zofenopril calcium salt having a content in polymorph B lower than 15%.

3. A pharmaceutical composition containing as active ingredient polymorph A of zofenopril calcium salt having a content in polymorph B lower than 7%.

4. A method for preparing medicaments for the treatment of essential hypertension, cardiac decompensation and acute myocardial infarction, comprising:

adding substantially pure zofenopril calcium salt Polymorphin A to said medicament.

5. A method for preparing medicaments for the treatment of essential hypertension, cardiac decompensation and acute myocardial infarction, comprising:

adding substantially pure zofenopril calcium salt Polymorphin A having a content in polymorph B lower than 15% to said medicament.

6. A method for preparing medicaments for the treatment of essential hypertension, cardiac decompensation and acute myocardial infarction, comprising:

adding substantially pure zofenopril calcium salt polymorph A having a content in polymorph B lower than 7% to said medicament.

* * * * *